(12) United States Patent
Moser et al.

(10) Patent No.: US 6,444,431 B1
(45) Date of Patent: Sep. 3, 2002

(54) ANGIOSTATIN RECEPTOR

(75) Inventors: Tammy L. Moser, Durham; Salvatore V. Pizzo, Bahama, both of NC (US); Mary S. Stack, Chicago, IL (US)

(73) Assignees: Duke University, Durham, NC (US); Northwestern University, Evanston, IL (US)

( * ) Notice: Subject to any disclaimer, the term of this patent is extended or adjusted under 35 U.S.C. 154(b) by 0 days.

(21) Appl. No.: 09/314,159

(22) Filed: May 19, 1999

Related U.S. Application Data

(60) Provisional application No. 60/086,155, filed on May 19, 1998, and provisional application No. 60/124,070, filed on Mar. 12, 1999.

(51) Int. Cl.$^7$ ...................... G01N 33/53; G01N 33/567; G01N 33/574; C12Q 3/00; C01K 1/00
(52) U.S. Cl. .............................. 435/7.2; 435/4; 435/7.1; 435/7.23; 530/350; 530/387.1
(58) Field of Search ............................. 530/350, 387.1; 436/500; 435/4, 7.1, 7.2, 7.21, 7.23

(56) References Cited

U.S. PATENT DOCUMENTS

| | | |
|---|---|---|
| 5,681,372 A | 10/1997 | Magits |
| 5,837,682 A | 11/1998 | Folkman et al. |
| 5,945,403 A | 8/1999 | Folkman et al. |
| 6,024,688 A | 2/2000 | Folkman et al. |
| 6,110,722 A | 8/2000 | Hillman et al. |

FOREIGN PATENT DOCUMENTS

| | | |
|---|---|---|
| WO | WO 99/66038 | 12/1999 |
| WO | WO 00/32631 | 6/2000 |

OTHER PUBLICATIONS

Boyer, "The ATP Synthase–A Splendid Molecular Machine", Annu. Rev. Biochem. 66:717–749 (1997).

Kataoka et al, "Nucleotide sequence of a cDNA for the α subunit of human mitochondrial ATP synthase", Biochimica et Biophysica Acta 1089:393–395 (1991).

Rao et al, "The Defective Proton–ATPase of *uncA* Mutants of *Escherichia coli*. ATP–Binding and ATP–Induced Conformational Change in Mutant α–Subunits", Archives of Biochemistry and Biophysics 255(2):309–315 (1987).

Das et al, "A Novel Ligand in Lymphocyte–mediated Cytotoxicity: Expression of the β Subunit of $H^+$ Transporting ATP Synthase on the Surface of Tumor Cell Lines", J. Exp. Med. 180:273–281 (1994).

Moreno et al, "Vascular–type $H^+$–ATPase regulates cytoplasmic pH in Toxoplasma gondii tachyzoites", Biochem. J. 330:853–860 (1998).

Elston et al, "Energy transduction in ATP synthase", Nature 39:510–513 (1998).

Miles et al, "Role of Cell–Surface Lysines in Plasminogen Binding to Cells: Identification of α–Enolase as a Candidate Plasminogen Receptor", Biochemistry 30(6):1682–1691 (1991).

*Primary Examiner*—Anthony C. Oaputa
*Assistant Examiner*—Jennifer Hunt
(74) *Attorney, Agent, or Firm*—Nixon & Vanderhye P.C.

(57) ABSTRACT

The present invention relates, in general, to an angiostatin receptor and, in particular, to an angiostatin receptor present on cellular plasma membranes. More particularly, the present invention relates to the human angiostatin receptor, ATP synthase, or subunit or portion thereof, and to the use thereof in assays designed to screen compounds for their ability to serve as agonists or antagonists of human angiostatin. The invention further relates to nucleic acid sequences encoding ATP synthase, or subunit or portion thereof, and to host cells transformed therewith. The invention also relates to antibodies specific for ATP synthase.

10 Claims, 9 Drawing Sheets

ANGIOSTATIN RECEPTOR

The present application claims priority from Provisional Application No. 60/086,155, filed May 19, 1998, and Provisional Application No. 60/124,070, filed Mar. 12, 1999, the entire contents of both applications being incorporated herein by reference.

TECHNICAL FIELD

The present invention relates, in general, to an angiostatin receptor and, in particular, to an angiostatin receptor present on cellular plasma membranes. More particularly, the present invention relates to the human angiostatin receptor, ATP synthase, or subunit or portion thereof, and to the use thereof in assays designed to screen compounds for their ability to serve as agonists or antagonists of human angiostatin. The invention further relates to nucleic acid sequences encoding ATP synthase, or subunit or portion thereof, and to host cells transformed therewith. The invention also relates to antibodies specific for ATP synthase.

BACKGROUND

Tumor growth requires persistent blood vessel generation in the process of angiogenesis. If vascularization is prevented, tumor growth is dramatically impaired and the tumor size is restricted. Modulation of endogenous angiogenic inhibitors thus plays an important role in tumor development. Angiostatin, a proteolytic fragment of plasminogen, is a potent inhibitor of angiogenesis and the growth of tumor cell metastases (O'Reilly et al, Cell 79:315–328 (1994)). Angiostatin can be generated in vitro by limited proteolysis of plasminogen (Sottrup-Jensen et al, Progress in Chemical Fibrinolysis and Thrombolysis 3:191–209 (1978)) resulting in a 38 kDa plasminogen fragment ($Val^{79}$-$Pro^{353}$). Although the enzymatic mechanism by which angiostatin is generated in vivo is unknown, recent studies have demonstrated that the cleavage of plasminogen to angiostatin can be catalyzed by a serine proteinase (Gately et al, Cancer Research 36:4887–4890 (1996)) and a macrophage metalloelastase (Dong et al, Cell 88:801–810 (1997)). Generation of angiostatin from reduction of plasmin has also been shown in vitro (Gately et al, PNAS 94:10868–10872 (1997)) and in Chinese hamster ovary and human fibrosarcoma cells (Stathakis et al, JBC 272(33):20641–20645 (1997)).

Cellular receptors for plasminogen have previously been demonstrated on human umbilical vein endothelial cells (HUVEC) and are believed to function in the regulation of endothelial cell activities, including angiogenesis (Hajjar et al, J. Biol. Chem. 261(25):11656–11662 (1986), Hajjar et al, JBC 269(3):21191–21197 (1994)). Receptors for plasminogen are also expressed in high numbers on tumor cells, where they have been identified as critical for tumor invasion. Proteins normally found in the cytoplasm have also been shown on cell surface membranes and serve as plasminogen binding sites (Miles et al, Biochemistry 30:1682–1691 (1991)).

The present invention results from the demonstrations that plasminogen and angiostatin bind to distinct sites on cellular plasma membranes and that ATP synthase is the angiostatin binding protein. These findings make possible assays that can be used to screen compounds for their ability to modulate angiostatin activities. Compounds so identified have profound usefulness as therapeutic agents.

SUMMARY OF THE INVENTION

The present invention relates to an angiostatin receptor present on cellular plasma membranes. More particularly, the present invention relates to the human angiostatin receptor, ATP synthase, and to the use thereof, or of subunits or portions thereof, in assays designed to screen compounds for their ability to modulate angiostatin activities. The invention further relates to a nucleic acid sequences encoding ATP synthase, or subunit or portion thereof, and to host cells transformed therewith. The invention also relates to antibodies specific for ATP synthase.

BRIEF DESCRIPTION OF THE DRAWINGS

FIG. 1A. $^{125}$I-labeled plasminogen binding was concentration-dependent and saturable with an apparent dissociation constant ($K_d$) of 158 nM and 870,000 sites/cell. FIG. 1B. Binding to HUVEC with $^{125}$I-labeled angiostatin was concentration-dependent and saturable with a $K_d$ of 245 nM and 38,000 sites/cell. Error bars represent standard deviation.

In FIG. 4D, HUVEC demonstrate specific, saturable binding of antibodies directed against the α subunit of ATP synthase. The mean relative fluorescence of HUVEC incubated with pre-immune rabbit serum subtracted from the mean relative fluorescence of HUVEC incubated with the same volume of anti-α ATP synthase gave the mean relative fluorescence resulting from the specific binding of antibodies directed against the α subunit of ATP synthase on the HUVEC surface.

FIG. 5A, HUVEC under epi-illumination showing immunofluorescent surface staining for the α subunit of ATP synthase. FIG. 5B, Same field of HUVEC under visible light. FIG. 5C, Human dermal microvascular endothelial cells also showed immunofluorescent surface staining for the α subunit of ATP synthase. Control experiments were performed with FIG. 5D, pre-immune serum and FIG. 5E, secondary antibody alone. FIG. 5F, HUVEC were permeabilized by acetone fixation prior to adding antibodies for the α subunit of ATP synthase.

FIG. 7A. Coomassie stain of Immobilon membrane containing the α subunit of human ATP synthase. FIG. 7B. Binding of 0.5 μM $^{125}$I-labeled angiostatin. FIG. 7C. Binding of 0.5 μM $^{125}$I-labeled angiostatin in the presence of a 250-fold molar excess of unlabeled angiostatin. Binding of angiostatin is inhibited by ~56%. FIG. 7D. Binding of 0.5 μM $^{125}$I-labeled angiostatin in the presence of a 2500-fold molar excess of unlabeled plasminogen. Binding of angiostatin is not inhibited. FIG. 7E. Binding of 0.5 μm $^{125}$I-labeled plasminogen to the α subunit of human ATP synthase. Plasminogen did not bind to the recombinant α subunit of ATP synthase, however, it did bind the annexin II control (as shown in FIG. 3).

DETAILED DESCRIPTION OF THE INVENTION

Figure 1A:
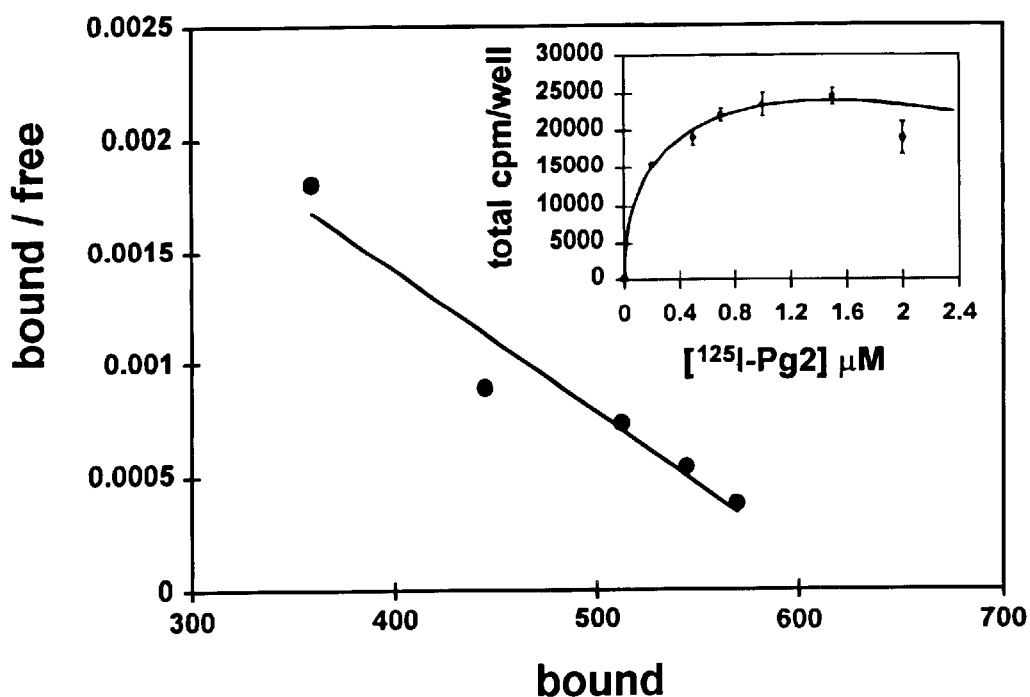
FIGS. 1A and 1B. Direct binding assay and Scatchard analysis of plasminogen and angiostatin with endothelial cells. HUVEC were plated at a density of 10,000 cells/well and incubated with increasing concentrations of $^{125}$I-labeled-plasminogen or angiostatin.

The present invention results from the demonstration that plasminogen and angiostatin bind to distinct sites on the surface of endothelial cells, annexin II and ATP synthase, respectively. The invention provides methods for identifying compounds that can be used to modulate the effects of angiostatin in vivo, including its inhibitory effects on angiogenesis and endothelial cell migration and proliferation.

In one embodiment, the present invention relates to methods of screening compounds for their ability to bind ATP synthase and thereby to function, potentially, as angiostatin agonists or antagonists. ATP synthase includes two principal domains, an asymmetric membrane-spanning $F_0$ portion containing a proton channel and a soluble $F_1$ portion containing three catalytic sites that cooperate in synthetic reactions. The $F_1$ region includes subunits α, β, γ, δ and ε. (See Elston et al, Nature 391:510 (1998).) The entire ATP synthase molecule can be used in the present assays or α subunit thereof can be used, for example, the α and/or β subunit, the angiostatin binding domain of ATP synthase can also be used, as can a fusion protein comprising the synthase, the subunit thereof or the angiostatinn binding domain thereof. The Examples that follow indicate that the α and β subunits of ATP synthase are present on the plasma membrane of endothelial cells. Further, the Examples indicate that angiostatin binds the α subunit. The α and β subunits present on cellular plasma membranes may be identical to those present on mitochondrial membranes or they may represent a truncated (e.g., N- or C-terminal truncated) form thereof. The binding assays of the invention include the use of any such truncated forms.

Binding assays of this embodiment invention include cell-free assays in which ATP synthase, or subunit thereof or angiostatin binding domain thereof (or fusion protein containing same), is incubated with a test compound (proteinaceous or non-proteinaceous) which, advantageously, bears a detectable label (e.g., a radioactive or fluorescent label). Following incubation, the ATP synthase, or subunit thereof or angiostatin binding domain thereof (or fusion protein), free or bound to test compound, can be separated from unbound test compound using any of a variety of techniques (for example, the ATP synthase (or subunit or binding domain of fusion protein) can be bound to a solid support (e.g., a plate or a column) and washed free of unbound test compound). The amount of test compound bound to ATP synthase, or subunit thereof or angiostatin binding domain thereof (or fusion protein), is then determined, for example, using a technique appropriate for detecting the label used (e.g., liquid scintillation counting and gamma counting in the case of a radiolabelled test compound or by fluorometric analysis).

Binding assays of this embodiment can also take the form of cell-free competition binding assays. In such an assay, ATP synthase, or subunit thereof or angiostatin binding domain thereof, or fusion protein containing same, is incubated with a compound known to interact with ATP synthase (e.g., angiostatin or ATP synthase binding portion thereof), which compound, advantageously, bears a detectable label (e.g., a radioactive or fluorescent label). A test compound (proteinaceous or non-proteinaceous) is added to the reaction and assayed for its ability to compete with the known (labeled) compound for binding to ATP synthase, or subunit thereof or angiostatin binding domain thereof (or fusion protein). Free known (labeled) compound can be separated from bound known compound, and the amount of bound known compound determined to assess the ability of the test compound to compete. This assay can be formatted so as to facilitate screening of large numbers of test compounds by linking the ATP synthase, or subunit thereof or angiostatin binding domain thereof (or fusion protein), to a solid support so that it can be readily washed free of unbound reactants. A plastic support, for example, a plastic plate (e.g., a 96 well dish), is preferred.

ATP synthase, or subunit thereof or angiostatin binding domain thereof (or fusion protein), suitable for use in the cell-free assays described above can be isolated from natural sources (e.g., membrane preparations) or prepared recombinantly or chemically. The ATP synthase, or subunit thereof or angiostatin binding domain thereof, can be prepared as a fusion protein using, for example, known recombinant techniques. Preferred fusion proteins include a GST (glutathione-S-transferase) moiety, a GFP (green fluorescent protein) moiety (useful for cellular localization studies) or a His tag (useful for affinity purification). The non-ATP synthase moiety can be present in the fusion protein N-terminal or C-terminal to the ATP synthase, subunit or binding domain.

As indicated above, the ATP synthase, or subunit thereof or angiostatin binding domain thereof, or fusion protein, can be present linked to a solid support, including a plastic or glass plate or bead, a chromatographic resin (e.g., Sepharose), a filter or a membrane. Methods of attachment of proteins to such supports are well known in the art and include direct chemical attachment and attachment via a binding pair (e.g., biotin and avidin or biotin and streptavidin). It will also be appreciated that, whether free or bound to a solid support, the ATP synthase, or subunit thereof or angiostatin binding domain thereof, or fusion protein, can be unlabeled or can bear a detectable label (e.g., a fluorescent or radioactive label).

The binding assays of the invention also include cell-based assays in which ATP synthase, or subunit thereof or angiostatin binding domain thereof or fusion protein, is presented on a cell surface. Cells suitable for use in such assays include cells that naturally express ATP synthase and cells that have been engineered to express ATP synthase (or subunit thereof or angiostatin binding domain thereof or fusion protein comprising same). The cells can be normal or tumorigenic. Advantageously, cells expressing human ATP synthase are used. Examples of suitable cells include procaryotic cells (e.g., bacterial cells (e.g., *E. coli*)), lower eucaryotic cells (e.g., yeast cells (e.g., hybrid kits from Promega (CG 1945 and Y190), and the strains YPH500 and BJ5457)) and higher eucaryotic cells (e.g., insect cells and mammalian cells (e.g., endothelial cells, including bovine aortic endothelial cells (BAEC), bovine adrenal medulla endothelial cells (BAMEC), murine endothelial cells $CP_y$-4-1, HUVEC or any human endothelial cell line, or cells such as human lung carcinoma cells (e.g., A549 cells))).

Cells can be engineered to express ATP synthase (advantageously, human ATP synthase, or subunit thereof or angiostatin binding domain thereof, or fusion protein that includes same) by introducing into a selected host an expression construct comprising a sequence encoding ATP synthase, or subunit thereof or angiostatin binding domain thereof or fusion protein, operably linked to a promoter. A variety of vectors and promoters can be used. For example, pET-24a(+) (Novagen) containing a T7 promoter is suitable for use in bacteria, likewise, pGEX-5X-1. Suitable yeast expression vectors include pYES2 (Invitron). Suitable baculovirus expression vectors include p2Bac (Invitron). Suitable mammalian expression vectors include pBK/CMV (Stratagene). Introduction of the construct into the host can be effected using any of a variety of standard transfection/transformation protocols (see Molecular Biology, A Laboratory Manual, second edition, J. Sambrook, E. F. Fritsch and T. Maniatis, Cold Spring Harbor Press, 1989). Cells thus produced can be cultured using established culture techniques suitable for the involved host. Culture conditions can be optimized to ensure expression of the ATP synthase (or subunit, binding domain or fusion protein) encoding sequence.

While for the cell-based binding assays the ATP synthase (or subunit, binding domain or fusion protein) can be expressed on a host cell membrane (e.g., on the surface of the host cell), for other purposes the encoding sequence can be selected so as to ensure that the expression product is secreted into the culture medium.

The cell-based binding assays of the invention can be carried out by adding test compound (advantageously, bearing a detectable (e.g., radioactive or fluorescent) label), to medium in which the ATP synthase (or subunit thereof or angiostatin binding domain thereof or fusion protein containing same) expressing cells are cultured, incubating the test compound with the cells under conditions favorable to binding and then removing unbound test compound and determining the amount of test compound associated with the cells.

Identification of ATP synthase on a cell membrane (e.g., on the cell surface) can be made using techniques such as those in the Examples that follow (e.g., the cell surface can be biotin labeled and the protein followed by a fluorescent tag). Membrane associated proteins (e.g., cell surface proteins) can also be analyzed on a Western blot and the bands subjected to mass spectroscopy analysis. For example, a fluorescently tagged antibody can be used with permeabilzed cells which cells can then be probed with another fluorescently tagged protein. Each tag can be monitored at a different wavelength, for example, using a confocal microscope to demonstrate co-localization.

As in the case of the cell-free assays, the cell-based assays can also take the form of competitive assays wherein a compound known to bind ATP synthase (and preferably labelled with a detectable label) is incubated with the ATP synthase (or subunit thereof or angiostatin binding domain thereof or fusion protein comprising same) expressing cells in the presence and absence of test compound. The affinity of a test compound for ATP synthase can be assessed by determining the amount of known compound associated with the cells incubated in the presence of the test compound, as compared to the amount associated with the cells in the absence of the test compound.

It will be appreciated from a reading of this disclosure that the selectivity of a test compound for cell surface ATP synthase, as compared to mitochondrial ATP synthase, can be easily assessed. Compounds which, by virtue of their physicochemical properties, cannot diffuse across cellular membranes (and that are not natural or artificial ligands for cell transporters) can be considered selective for cell surface ATP synthase. For example, compounds that bind cell surface ATP synthase but are positively charged can thereby be prevented from diffusing across membranes.

A test compound identified in one or more of the above-described assays as being capable of binding to ATP synthase can, potentially, mimic or enhance the effects of angiostatin on angiogenesis, cellular migration, proliferation and pericellular proteolysis or, potentially, antagonize the effects of angiostatin, for example, by precluding angiostatin from binding its receptor. To determine the specific effect of any particular test compound selected on the basis of its ability to bind ATP synthase (or inhibit (competitively or non-competively) angiostatin binding to ATP synthase), assays can be conducted to determine, for example, the effect of various concentrations of the selected test compound on activity, for example, cell (e.g., endothelial cell) proliferation, metabolism or cytosolic/cytoplasmic pH. (Assays can be conducted to determine the effect of test compounds on ATP synthase (and ATPase) activity using standard enzyme assay protocols.)

Cell proliferation can be monitored by measuring uptake of labeled (e.g., radioactively (e.g., $^3$H, $^{51}$C, $^{14}$C), for example, fluorescently (e.g., CYQUANT (Molecular Probes)) or colorimetrically (e.g., βrdU (Boehringer Mannheim or MTS (Promega)), bases into cellular nucleic acids. Cytosolic/cytoplasmic pH determinations can be made with a digital imaging microscope using substrates such as BCECF (bis(carboxyethyl)-carbonyl fluorescein) (Molecular Probes, Inc.) A test compound that reduces or replaces the concentration of angiostatin required to inhibit cellular proliferation or lower intracellular pH can be expected to do so by acting as an angiostatin agonist. A test compound that enhances cellular proliferation in the presence of angiostatin (or functional portion thereof or functional equivalent thereof) can be expected to do so by acting as an angiostatin antagonist. A test compound that raises intracellular pH in the presence of angiostatin (or functional portion thereof or functional equivalent equivalent thereof) may do so by acting as an angiostatin antagonist. These functional assays can also be conducted in the absence of angiostatin (i.e., test compound alone), with angiostatin (or functional portion thereof or functional equivalent equivalent thereof) run as a separate control. A test compound that, for example, modulates intracellular pH in the absence of angiostatin can be an angiostatin agonist or antagonist.

Other types of assays that can be carried out to determine the effect of a test compound on angiostatin binding to ATP synthase include the Lewis Lung Carcinoma assay (O'Reilly et al, Cell 79:315 (1994)) and extracellular migration assays (Boyden Chamber assay: Kleinman et al, Biochemistry 25:312 (1986) and Albini et al, Can. Res. 47:3239 (1987)).

Das et al (J. Exp. Med. 180:273 (1994)) have reported the presence of the β subunit of H$^+$ transporting ATP synthase on the plasma membrane of human tumor cell lines. The present demontration of the α subunit of ATP synthase on plasma membranes, and the binding thereto of angiostatin, indicates that angiostatin may be directly involved in effecting cytolysis, for example, of tumor cells. The binding of angiostatin to its receptor may result in the transport of protons across plasma membranes and into cells with the result being cytolysis by osmotic shock. Accordingly, the present invention includes within its scope methods of screening compounds for their ability to modulate the effect of angiostatin on proton pumping that results from the binding of angiostatin to its receptor. In one such assay, cells that express ATP synthase (or subunit (e.g., α or β) or portion thereof) are incubated with the test compound in the presence of angiostatin (or functional portion thereof or functional equivalent thereof) and the influx of protons into the cells determined and compared to the influx of protons observed in the absence of the test compound. Compounds that reduce the concentration of angiostatin (or functional portion thereof or functional equivalent thereof) necessary to effect a particular level of proton influx can be expected to do so by acting as a angiostatin agonist. Compounds that reduce the amount of angiostatin-induced proton pumping observed can be expected to do so by acting as an angiostatin antagonist. The amount of proton pumping can be determined using any of a variety of approaches, including using cells preloaded with a pH sensitive reporter (for example, BCECF can be used to measure pH (Misra et al, Biochem. J. 309:151 (1995)) and monitoring the effect of the test compound on the reporter. Alternatively, the effect of a test compound on proton pumping can be determined by monitoring cell lysis using, for example, a chromium 51 release assay (McManus et al, Exper. Lung Res. 15:849 (1989); Zucker et al, Res. Comm. Chem. Path. Pharm. 39:321 (1983)).

In addition to the various approaches described above, assays can also be designed so as to be monitorable colorometrically or using time-resolved fluorescence.

In another embodiment, the invention relates to compounds identified using the above-described assays as being capable of binding to ATP synthase (and/or inhibiting angiostatin from binding to ATP synthase (competively or non-competitively) and/or modulating the angiostatin effects on cellular bioactivities and/or modulating ATP synthase activity. Such compounds can include novel small molecules (e.g., organic compounds (for example, organic compounds less than 500 Daltons), and novel polypeptides, oligonucleotides, as well as novel natural products (preferably in isolated form) (including alkyloids, tannins, glycosides, lipids, carbohydrates and the like). Compounds that mimic or enhance angiostatin activities can be used to inhibit angiogenesis, for example, in tumor bearing patients and in patients suffering from vascular related retinopathies (including diabetic) and Terigium. Other diseases in which angiogenesis is a significant component of tissue pathology include rheumatoid arthritis and keloid formation. Compounds that inhibit angiostatin activities can be used to promote angiogenesis in conditions of vascular insufficiency, including ischemic heart disease, peripheral vascular disease, thromboembolic disease, stroke and vasculitities (Buerger's disease, Wegener's granulomatosis, and Giant Cell Arteritis). Such compounds can also be used at wound sites to promote healing, and at sites of transplantation and grafting (e.g., skin grafting). Other diseases/disorders amenable to treatment using compounds selected in accordance with the above-described assays include obesity, osteo-arthritis, vascular diseases/disorders of the eye, including diabetic retinopathy, macular degeneration, retinopathy of prematurity, corneal inflammation, and viral infections, as well as psoriasis, spinal cord injuries, and other diseases and disorders that can be expected to benefit from intervention of vascularization.

The compounds identified in accordance with the above assays can be formulated as pharmaceutical compositions. Such compositions comprise the compound and a pharmaceutically acceptable diluent or carrier. The compound can be present in dosage unit form (e.g., as a tablet or capsule) or as a solution, preferably sterile, particularly when administration by injection is anticipated. The compound can also be present as a cream, gel or ointment, for example, when topical administration is preferred. The dose and dosage regimen will vary, for example, with the patient, the compound and the effect sought. Optimum doses and regimens can be determined readily by one skilled in the art.

In a specific embodiment, the invention relates to a method of antagonizing the effect of angiostatin in a patient by administering ATP synthase, or soluble, angiostatin binding portion thereof. The ATP synthase, or portion thereof, suitable for use in this method can be prepared recombinantly or chemically and can be formulated with an acceptable carrier (including a liposome) as a pharmaceutical composition. The ATP synthase, or portion thereof, can be present as a fusion protein, for example, fused to the heavy chain of IgG. The ATP synthase, or portion thereof, can be derivatized (e.g., with polyethylene glycol) so as to modify its half life in vivo. The method of this embodiment finds application, for example, in wound healing.

In another embodiment, the invention relates to antibodies specific for ATP synthase, and antigen binding fragments thereof, including $F(ab)_2'$ or $F(ab)$ fragments. The antibodies can be monoclonal or polyclonal and can be prepared using standard techniques (Harlow and Lane Antibodies, A Laboratory Manual, (1988) Cold Spring Harbor Laboratories). The antibodies can be used in ATP purification protocols or the antibodies can be formulated as pharmaceutical compositions and used therapeutically to mimic or enhance the effects of angiostatin on endothelial cells or to antagonize such effects.

In yet a further embodiment, the invention relates to kits, for example, kits suitable for conducting assays described herein. Such kits can include ATP synthase, or subunit thereof or angiostatin binding domain thereof, or fusion protein comprising same, and/or angiostatin. These components can bear a detectable label. The kit can include an ATP synthase-specific or angiostatin-specific antibody. Plasminogen can also be present. The kit can include any of the above components disposed within one or more container means. The kit can further include ancillary reagents (e.g., buffers) for use in the assays.

In another embodiment, the present invention relates to methods of diagnosis that are based, for example, on assays for the binding of angiostatin to ATP synthase. Such methods make possible the identification of patients suffering from diseases, disorders or conditions associated with abnormal angiogenesis.

The demonstration that ATP synthase is the angiostatin binding protein, and the resulting availability of methods of identifying agents that can be used to modulate the effects of angiostatin, make it possible to determine which individuals will likely be responsive to particular therapeutic strategies. Treatment strategies for individuals suffering from a disease, disorder or condition associated with abnormal angiogenesis can thus be designed more effectively and with greater predictability of a successful result. Thus, for a given clinical disease that is associated both with abnormal angiogenesis and that is of polygenic (non-Mendelian) origin, one would select that genotype that is implicated not only in the disease, but also in that variant of the disease that is associated with abnormal angiogenesis and proceed to screen, via a diagnostic procedure, all future patients having the same genotype in order to choose that therapeutic strategy most associated with a successful outcome or least associated with a toxic side effect, for that genotype.

Certain aspects of the present invention are described in greater detail in the non-limiting Examples that follow.

EXAMPLES

The following experimental details are referenced in the specific Examples that follow.
Protein Purification
Plasminogen was purified from human plasma by affinity chromatography and separated into isoforms 1 and 2 as previously described (Deutsch et al, Science 170:1095 (1970), Gonzalez-Gronow et al, Biochemistry 23:190–194 (1984)). Based on kinetic and electrophoretic analysis, all plasminogen preparations were shown to be plasmin-free. The concentration of plasminogen was determined spectrophotometrically at 280 nm using an $A^{1\%}/1$ cm value of 1.67 and a molecular mass of 92 kDa for Glu$^1$-plasminogen (Castellino et al, Chem. Rev. 81:431 (1981)). Human plasminogen kringles 1–3 (angiostatin) were purified as previously described (Sottrup-Jensen et al, Progress in Chemical Fibrinolysis and Thrombolysis 3:191–209 (1978)). The concentration of angiostatin was determined spectrophotometrically at 280 nm using an $A^{1\%}/1$ cm value of 0.8 and a molecular mass of 38 kDa (Sottrup-Jensen et al, Progress in Chemical Fibrinolysis and Thrombolysis 3:191–209 (1978)). Protein endotoxin levels were <50.0 pg endotoxin/ml as assessed by Pyrotell Limulus amebocyte lysate clotting times (Associates of Cape Cod, Woods Hole, Mass.)
Cell Culture
Primary human umbilical vein endothelial cells (HUVEC) were grown as previously described (Morales et al, Circulation 91:755–763 (1995)) in 150 mm petri dishes and retained for up to 6 passages. Human dermal microvascular endothelial cells (HMVEC) were obtained from Clonetics (San Diego, Calif.), grown according to specifications and retained for up to 6 passages. A549 (human lung carcinoma) cells were obtained from ATCC (Rockville, Md.) and grown according to specifications. For all experiments cells were detached by incubation with PBS containing 2 mM EDTA, pH 7.4.
Antibody Purification
Antibody to His-tagged recombinant α-subunit ATP synthase was generated in rabbits by intranodal injection (Covance Laboratories, Vienna, Va.). Production bleeds were centrifuged and the serum obtained was ammonium sulfate precipitated. The precipitate was resuspended in PBS/0.5M NaCl, pH 7.5 and passed over Protein A-Sepharose (Sigma, St. Louis, Mo.), plasminogen-Sepharose and α-subunit ATP synthase-Sepharose columns (CNBr coupling, Pharmacia Amersham, Piscataway, N.J.). Each column was eluted with 20 mM glycine, pH 2.5. Neutralized IgG fractions were tested by immunodiffusion, ELISA and Western blotting. Antibody to the α-subunit of ATP synthase showed no cross-reactivity with plasminogen or other proteins by Western blot analysis. Polyclonal antibody obtained from Dr. A. E. Senior (Rochester Medical Center, Rochester, N.Y.) directed against the α subunit of ATP synthase from *E. coli* was characterized by ELISA and Western blot analysis and showed no cross-reactivity with other proteins in the $F_1$ portion or *E. coli* cell membranes (Perlin et al, Archives of Biochem. and Biophys. 236(2):603–611 (1985), Rao et al, Archives of Biochem. and Biophys. 255(2):309–315 (1987)).
Binding Assays
Ligands were radioiodinated using Iodobeads™ (Pierce), repurified on L-lysine-Sepharose, eluted with 100 mM ε-aminocaproic acid (EACA) and dialyzed in PBS, pH 7.0, before use in binding assays. HUVEC were plated at a density of 5000 or 10,000 cells/well and incubated with increasing concentrations of $^{125}$I-labeled ligand in media containing 1% bovine serum albumin (BSA) for 1 h at 4° C. in 96-well plates. Wells were washed and remaining bound radioactivity was quantified using an LKB 1272 γ-radiation counter. Non-specific binding was measured in the presence of excess unlabeled ligand.
Membrane Purification
Plasma membrane extracts from NHS-biotin labeled HUVEC were prepared by 300 psi Parr bomb nitrogen cavitation and ultracentrifugation (Young et al, J. Biol. Chem. 270(3):999–1002 (1995)). Membrane extracts were incubated with plasminogen-Sepharose or angiostatin-Sepharose columns in an inhibitor cocktail buffer (Young et al, J. Biol. Chem. 270(3):999–1002 (1995)). Each Sepharose column was eluted with 50 mM Tris/100 mM EACA, pH 7.5, 50 mM Tris/1 M NaCl, pH 7.5, 50 mM Tris/7% DMSO and 20 mM glycine, pH 2.5 to account for all types of binding. The glycine eluates were dialyzed, lyophilized, electrophoresed on 5–15% gradient SDS-PAGE (Laemmli, Nature (London) 227:680–685 (1970)) and electroblotted onto Immobilon™ membrane (Matsudaira, J. Biol. Chem. 262:10035–10038 (1987)) prior to experiments to identify plasminogen and angiostatin binding proteins.

Mass Spectrometer Analysis

Plasma membrane proteins were separated on SDS-PAGE gels and the bands of interest were excised from the gels and digested in situ with trypsin. A portion (1/20) of each sample was analyzed by MALDI-MS and the obtained mass spectrometric peptide maps were used to identify the protein in the OWL Protein database release 29.6 (Mann et al, Biol. Mass Spectrom. 22:338–345 (1993), Pappin et al, Curr. Biol. 3:327–332 (1993)).

Flow Cytometry

HUVEC and A549 cells were resuspended in ice-cold staining buffer (HBSS, 1% BSA, 0.1% sodium azide) and incubated on ice for 30 min with either rabbit polyclonal anti-serum raised against α subunit ATP synthase derived from E. coli or pre-immune rabbit serum. Cells were washed with ice-cold staining buffer and pelleted in a microfuge at 4° C. This wash was repeated twice and the cells resuspended in ice-cold staining buffer prior to incubation on ice for 30 min in the dark with goat anti-rabbit IgG conjugated to fluorescein isothiocyanate (FITC). Following the final wash (as above), the cells were pelleted and fixed in 10% neutral buffered formalin at a density of $1\times10^6$ cells/ml. Control experiments were performed using antibody directed against the α subunit of ATP synthase which was preincubated with a 5-fold molar excess of recombinant α subunit ATP synthase protein. The mean relative fluorescence following excitation at a wavelength of 488 nm was determined for each sample on a FACScan flow cytometer (Becton-Dickenson) and analyzed with CellQuest software (Becton-Dickenson).

Immunofluorescence Microscopy

HUVEC and HMVEC were plated at $5\times10^5$ cells/ml on glass cover slips and allowed to adhere overnight. Cells were incubated at 4° C. for 1 h in PBS, pH7.0 containing 1% BSA with either rabbit polyclonal anti-serum raised against the α subunit of ATP synthase derived from E. coli, pre-immune rabbit serum, pre-immune IgG, or anti-rabbit IgG. Cells were washed and incubated at 4° C. for 1 h in the dark with goat anti-rabbit IgG conjugated to indocarbocyanine (Cy3) before washing and fixing in 4% paraformaldehyde. Immunofluorescence microscopy was performed using an Olympus BX-60 microscope (Olympus Corp., Lake Success, N.Y.).

Cloning of the α Subunit of ATP synthase

Poly A+ mRNA was isolated from HUVEC using Oligotex resin (Qiagen). RNA was reverse transcribed into single-stranded cDNA using AMV Reverse Transcriptase (Boeh. Mann.). The α subunit of ATP synthase was PCR amplified using Expand High Fidelity PCR system (Boeh. Mann.). The 1.7 kb PCR product was purified from a 0.8% TAE (tris-acetate/EDTA) agarose gel using a QIAEX II gel extraction kit. Restriction enzyme digests of the PCR fragment and vector pLE1 were carried out at 37° C. for 1 h. Both digests were passed over Qiaquick purification columns, then ligated overnight at 16° C. using T4 DNA ligase. Competent E. coli DH5α (Gibco BRL) were transformed with the ligation mixture, plated on 2xYT agarose plates and grown overnight at 37° C. Colonies were screened for the insert via restriction enzyme digest and DNA sequencing.

Purification of the α Subunit of ATP Synthase

Competent E. coli BL21DE3 were transformed with the pLE1 vector containing the α-subunit, plated on 2xYT agarose and grown overnight at 37° C. 20 ml of 2xYT (YT=bacto-yeast tryptone) containing 50 μg/ml kanamycin were inoculated with one colony and grown overnight at 37° C. (200 rpm). A one liter culture (2xYT, 50 μg/ml kanamycin) was inoculated with 20 ml of the noninduced overnight culture and grown at 37° C. to an A of 0.6 at a wavelength of 600 nm. Isopropylthio-b-D-galactosidase (IPTG) was added to a final concentration of 1 mM and grown for an additional 3 hours. Cells were harvested by centrifugation at 8000 rpm for 10 minutes and stored overnight at −20° C. Lysates were prepared under denaturing conditions and batch purified using Qiagen Ni-NTA agarose (Qiagen). Resulting protein was dialyzed against PBS, pH 7.0 for use in all experiments.

Proliferation Assay

HUVEC were plated at a density of 5000 cells/well in media depleted of fetal calf serum overnight to allow the cells to become quiescent. Fresh media containing fetal calf serum was added to the wells along with angiostatin at a final concentration of 0.5, 0.75 and 1.0 μM. In some experiments, antibody directed against the α subunit of ATP synthase derived from E. coli was also added at a dilution of 1:10. MTS/PMS (3-(4,5-dimethylthiazol-2-yl)-5-(3-carboxymethoxyphenyl)-2-(4-sulfophenyl-2H-tetrazolium, inner salt/phenazine methosulfate)) solution was added after 24 hours and the absorbance of formazan was quantitated on a Thermomax™ plate reader at a wavelength of 490 nm according to the manufacturer's specifications (Promega, Madison, Wis.). The absorbance values used to calculate the percent proliferation of the cells ranged from 0.81 for untreated, 0.60 for treated and 0.47 for baseline quiescent cells.

EXAMPLE 1

Competition Binding Assay

To determine whether angiostatin blocks angiogenesis by competitive interaction with endothelial cell plasminogen receptors, the effects of angiostatin on the binding of plasminogen to endothelial cells were analyzed.

Figure 1B:
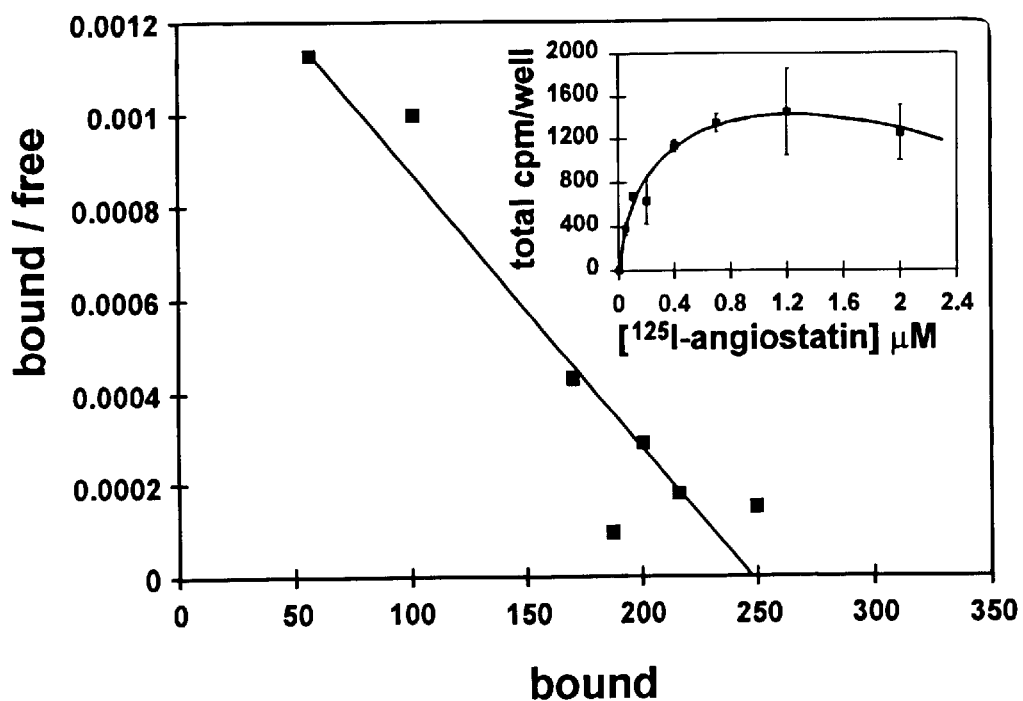
Figure 2:
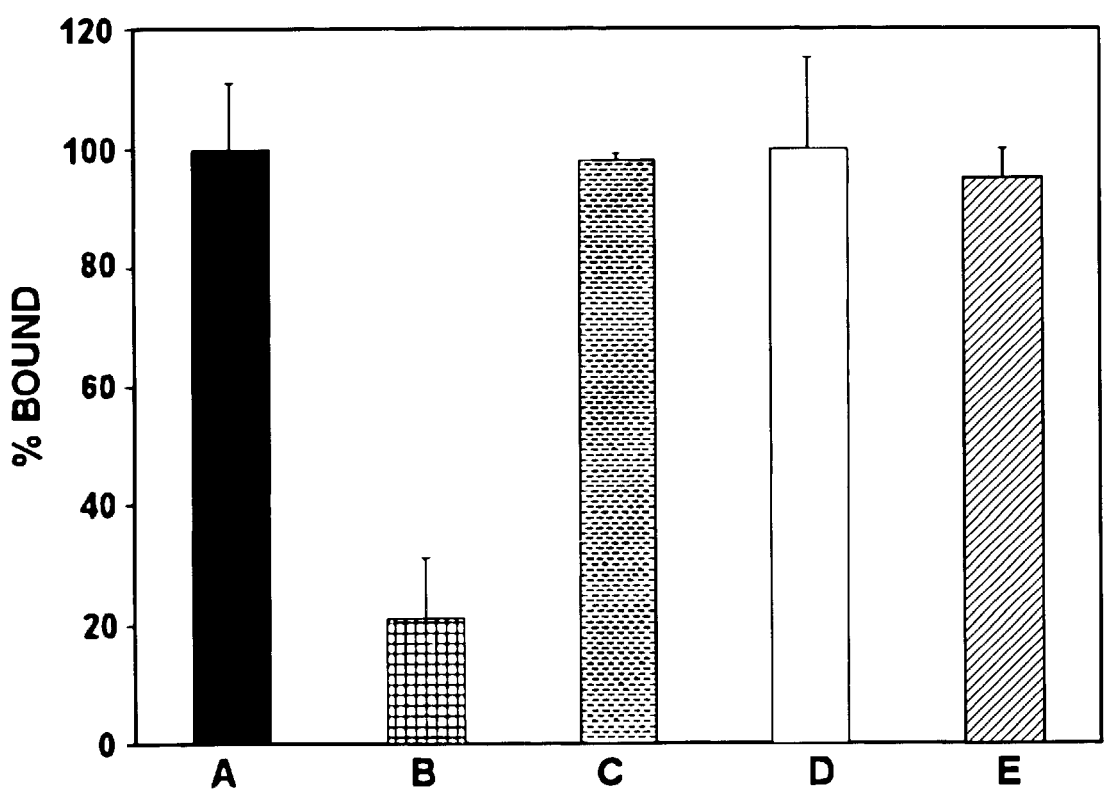
FIG. 2. Competition binding assay between plasminogen and angiostatin. HUVEC were plated at a density of 10,000 cells/well and incubated with 1.0 $\mu$M $^{125}$I-labeled plasminogen in the presence of 100-fold molar excess of unlabeled angiostatin for 1 h at 4° C. Cells were washed and the remaining radioactivity was quantified by γ-counting. (A) Total binding of 1.0 $\mu$M $^{125}$I-labeled plasminogen was designated as 100%. (B) Plasminogen binding is inhibited by ~80% in the presence of a 25-fold molar excess of unlabeled plasminogen. (C) Plasminogen binding was not inhibited in the presence of a 100-fold molar excess of unlabeled angiostatin suggesting distinct binding sites for each on the cells. Similar experiments using $^{125}$I-labeled angiostatin (D) showed no inhibition of binding in the presence of a 2-fold molar excess unlabeled plasminogen (E). Error bars represent standard deviation.

In control experiments, plasminogen bound to HUVEC in a concentration-dependent saturable manner with an apparent dissociation constant ($K_d$) of 158 nM and ~870,000 sites per cell (FIG. 1A), comparable to values previously reported (Hajjar et al, JBC 269(3):21191–21197 (1994)). Angiostatin also bound to HUVEC in a concentration-dependent saturable manner with a similar affinity ($K_d$ of 245 nM), with ~38,000 sites per cell (FIG. 1B). Binding studies utilizing $^{125}$I-labeled plasminogen and a 100-fold molar excess of unlabeled angiostatin demonstrated no inhibition of plasminogen binding (FIG. 2). Similar studies were performed using $^{125}$I-labeled angiostatin. Excess unlabeled plasminogen had little or no effect on angiostatin binding (FIG. 2). In contrast to plasminogen, binding of $^{125}$I-labeled angiostatin to HUVEC in the presence of 100 mM ε-aminocaproic acid (EACA) was only slightly inhibited, suggesting that binding of angiostatin to endothelial cells is not a lysine binding site dependant process. Together, these data indicate the presence of a distinct angiostatin binding site on HUVEC.

EXAMPLE 2

Purification of the Angiostatin Binding Site from Endothelial Cells

Figure 3:
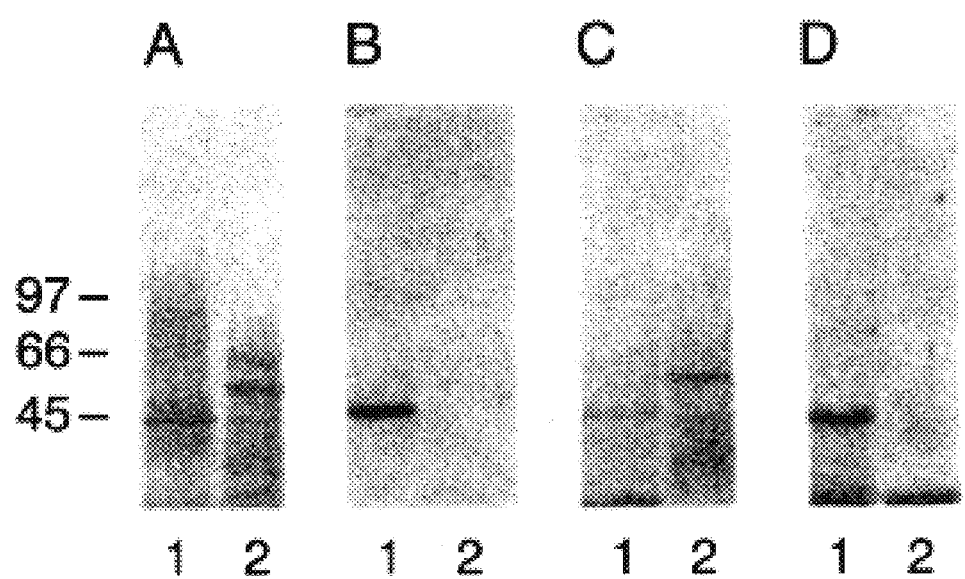
FIGS. 3A–3D. Affinity purification of plasminogen and angiostatin binding sites. SDS-PAGE containing membrane proteins were prepared and then analyzed by Western blotting. Membranes were incubated in 10 mM Tris-HCl, 0.15M NaCl, 0.05% NP40, pH 7.5 containing, FIG. 3A, streptavidin-alkaline phosphatase conjugate antibody, or, FIG. 3B, anti-annexin II antibody and developed using 5-bromo-4-chloroindol-3-yl-phosphate nitro blue tetrazolium. Membrane stained with Coomassie Brilliant blue, FIG. 3C, showing affinity purified membrane proteins. Membrane incubated with $^{125}$I-labeled plasminogen, FIG. 3D, showing binding to the plasminogen purified membrane and not the angiostatin. Lane 1 represents protein eluted from the plasminogen-Sepharose column. Lane 2 represents protein eluted from the angiostatin-Sepharose column. The relative molecular weights of α-ATP synthase and β-ATP synthase are ~55 and ~50 kDa, respectively.

The cell surface proteins involved in binding of plasminogen or angiostatin to HUVEC were identified by subjecting NHS-biotin labeled HUVEC plasma membranes to affinity chromatography on plasminogen-Sepharose or angiostatin-Sepharose. Two distinct bands were identified on Western blot analysis using streptavidin-alkaline phosphatase conjugate (FIG. 3A) or by Coomassie Brilliant blue stain (FIG. 3C). A companion blot, probed with an antibody to the known plasminogen receptor, annexin II, demonstrated immunologic cross-reactivity with the 44 kDa membrane protein isolated from the plasminogen-Sepharose column (FIG. 3B, lane 1), but not with the 55 kDa protein isolated from the angiostatin-Sepharose column (FIG. 3B, lane 2). Ligand blot analysis of the affinity purified plasma membranes using $^{125}$I-labeled plasminogen (FIG. 3D, lanes 1 and 2) demonstrated binding of plasminogen only to the 44 kDa protein and not to the 55 kDa specie. These data further evidence the fact that HUVEC contains an angiostatin binding site distinct from the plasminogen binding protein, annexin II.

EXAMPLE 3

Peptide Mass Fingerprinting of the Angiostatin Binding Site

To identify the unique angiostatin binding site component, the affinity-purified proteins were analyzed by amino-terminal sequencing, mass spectrometer analysis and peptide mass fingerprinting. Both the 44 and 55 kDa proteins were analyzed by reduced SDS-PAGE and digested with trypsin in situ (Matsui et al, Electrophoresis 18:409–417 (1997)). The resulting peptides were extracted and the mass of approximately 30 peptides was determined using a Bruker Reflex MALDI-TOF mass spectrometer, providing a unique signature by which to identify the protein by peptide mass searches (Mann et al, Biol. Mass Spectrom. 22:338–345 (1993), Pappin et al, J. Exp. Med. 180:273–281 (1994)). The 55 kDa angiostatin binding membrane protein was identified as the α/β subunits of ATP synthase (Table I), whereas the plasminogen binding protein was confirmed as annexin II. Although expression of the β subunit of ATP synthase has been reported on the surface of several tumor cell lines (Das et al, J. Exp. Med. 180:273 (1994)), this is the first evidence for surface expression of the subunits of ATP synthase on HUVEC.

TABLE I

Bruker Reflex MALDI-TOF mass spectrometer analysis of 55 kDa peptides

| | peptide mass (monoisotopic) | |
|---|---|---|
| Sequence | Measured (Da) | Calculated (Da) |
| QMSLLLR | 859.48 | 859.495 |
| AVDSLVPIGR | 1025.58 | 1025.587 |
| VGLKAPGIIPR | 1119.68 | 1119.713 |
| TIAMDGTEGLVR | 1261.40 | 1261.634 |
| ISVREPMQTGIK | 1357.70 | 1357.739 |
| IMNVIGEPIDER | 1384.68 | 1384.702 |
| AHGGYSVEAGVGER | 1405.66 | 1405.674 |
| FTQAGSEVSALLGR | 1434.73 | 1434.747 |
| TSIADTIINQKR | 1471.81 | 1471.836 |
| EAYPGDVEYLHSR | 1552.71 | 1552.731 |
| VALVYGQMNEPPGAR | 1600.79 | 1600.803 |
| TGAIVDVPVGEELLGR | 1623.87 | 1623.883 |
| LVLEVAQHLGESTVR | 1649.88 | 1649.910 |
| IMDPNIVGSEHYDVAR | 1814.85 | 1814.862 |
| VLDSGAPIKIPVGPETLGR | 1918.08 | 1918.089 |
| AIAELGIYPAVDPLDSTSR | 1986.99 | 1987.026 |
| IMNVIGEPIDERGPIKTK | 2009.10 | 2009.098 |
| IPSAVGYQPTLATDMGTMQER | 2265.06 | 2265.077 |
| EVAAFAQFGSDLDAATQQLLSR | 2337.15 | 2337.160 |

EXAMPLE 4

Figure 4A:
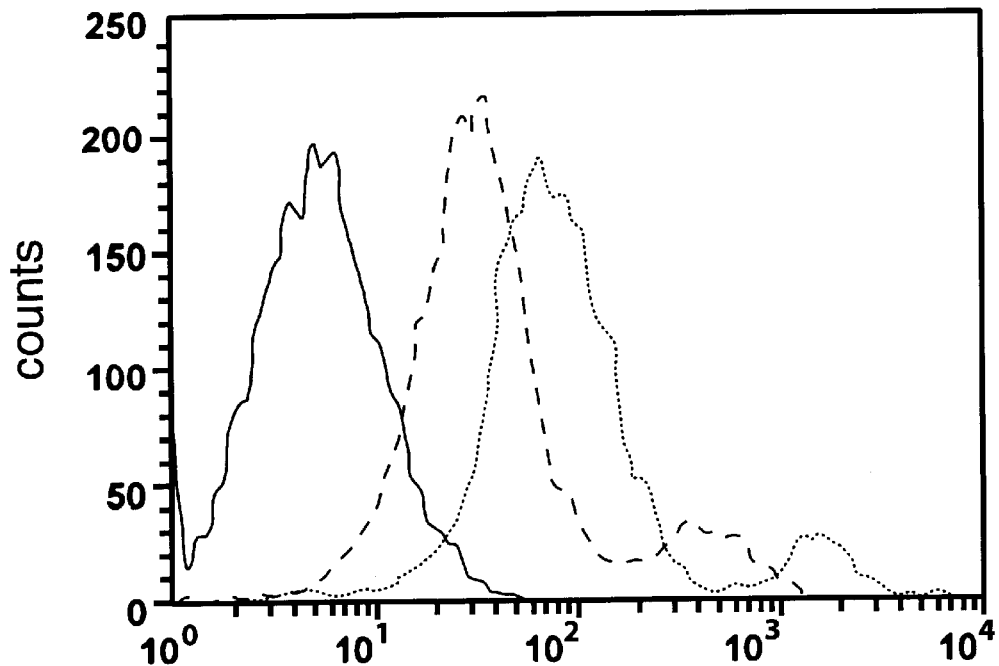
FIGS. 4A–4D. Binding of antibody directed against the α subunit of ATP synthase on the surface of HUVEC by flow cytometry. HUVEC were analyzed by FACScan Flow Cytometry. Histogram plots are shown for HUVEC (FIG. 4A) and A549 (FIG. 4B) where (· · ·) represents cells incubated with antibody directed against the α subunit of ATP synthase, (– – –) pre-immune serum and (—) secondary antibody only. Histogram plot of A549 shown in FIG. 4C are similar with (· · ·) representing antibody incubated with a 5-fold molar excess α ATP synthase protein.
Figure 4B:
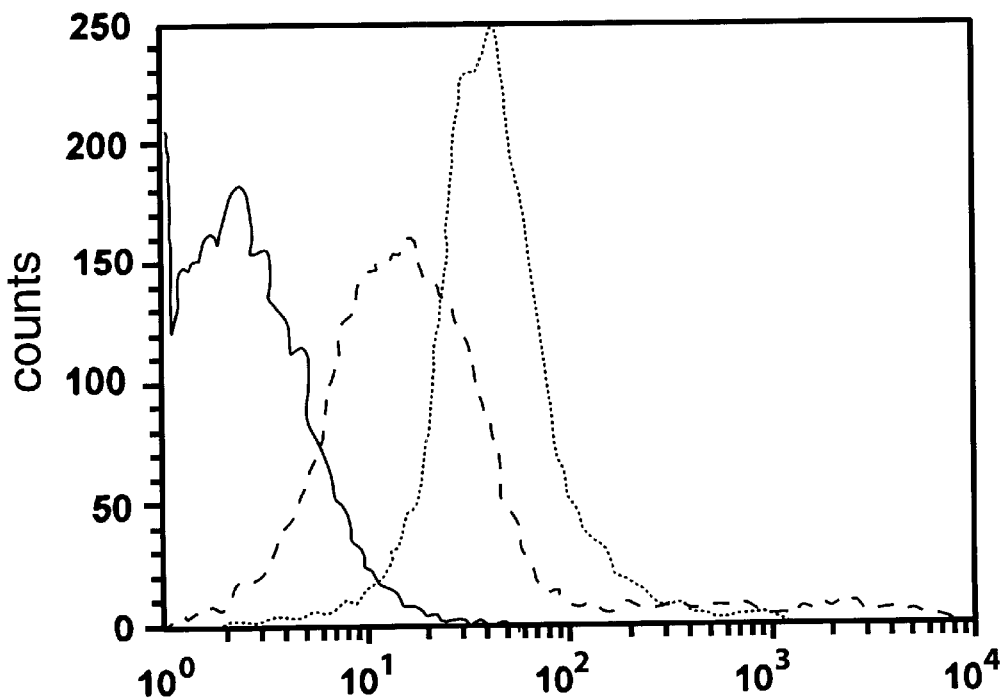
Figure 4C:
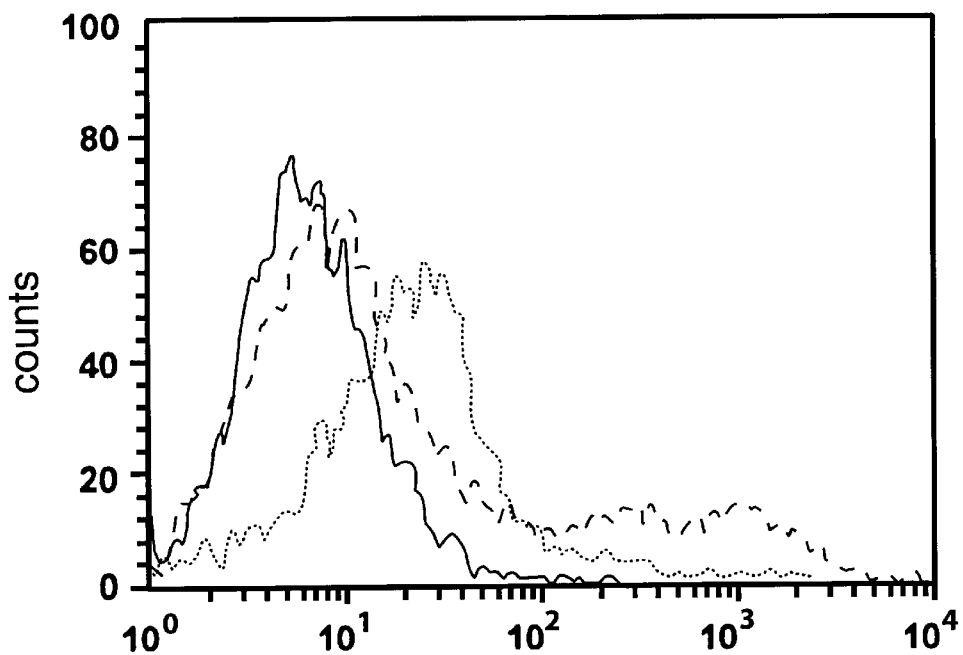
Figure 4D:
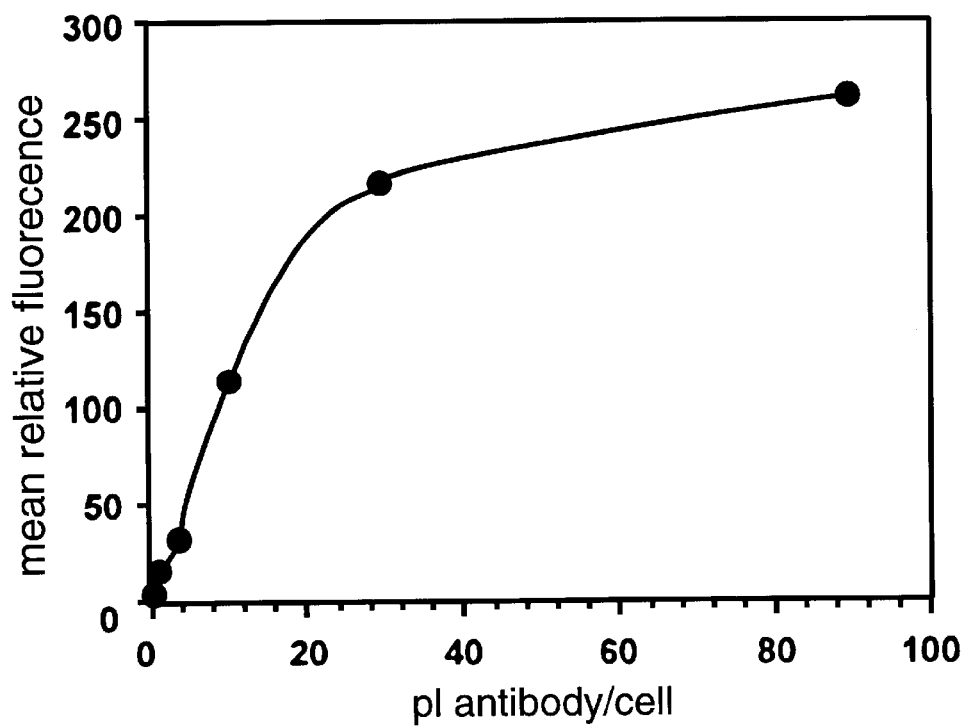

Binding of the α Subunit ATP Synthase Antibody to the Surface of HUVEC by Flow Cytometry and Immunofluorescence Microscopy To further confirm the surface localization of the ATP synthase, HUVEC were analyzed by flow cytometry and immunofluorescence microscopy. A rabbit polyclonal antiserum raised against the α subunit of ATP synthase from *E. coli* reacted with the cell membranes of HUVEC as determined by fluorescence-activated flow cytometry (FIG. 4). Control flow cytometry studies were performed using A549 cells which are known to express the α/β subunits of ATP synthase (Das et al, J. Exp. Med. 180:273–281 (1994)) (FIG. 4B). A549 cells were also analyzed with anti-α subunit ATP synthase antibody pre-incubated with a 5-fold molar excess of recombinant α subunit of ATP synthase protein and showed a decreased affinity for binding (FIG. 4C). HUVEC were incubated with increasing concentrations of antibody to determine saturation. FIG. 4D demonstrates specific, saturable binding of antibody directed against the α subunit of ATP synthase on HUVEC membranes.

Figure 5A:
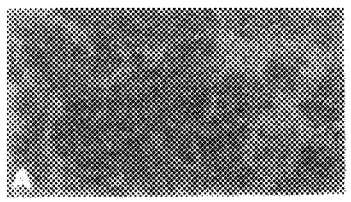
FIGS. 5A–5F. Immunofluorescence microscopy of ATP-synthase on HUVEC surface. HUVEC were incubated with rabbit polyclonal anti-serum raised against the α subunit of ATP synthase from E. coli.
Figure 5B:
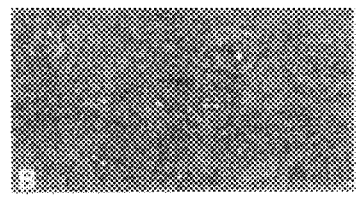
Figure 5C:
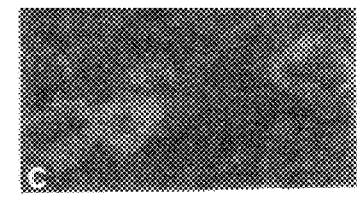
Figure 5D:
Figure 5E:
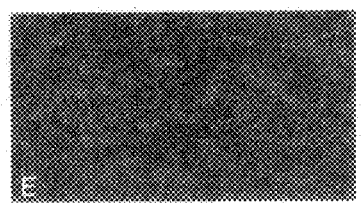
Figure 5F:
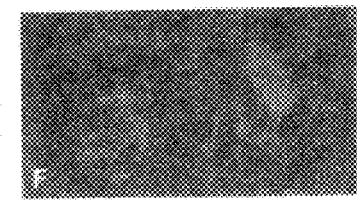

Immunofluorescence microscopy of HUVEC confirmed the surface-associated immunoreactivity of α subunit ATP synthase antibody on HUVEC cell membranes (FIG. 5A). Control experiments were performed with secondary antibody alone (FIG. 5D), pre-immune serum (FIG. 5E) and permeabilized HUVEC in the presence of anti-α subunit ATP synthase antibody (FIG. 5F). Human dermal microvascular endothelial cells also reacted with antiserum raised against the α subunit of ATP synthase (FIG. 5C).

EXAMPLE 5

Figure 6:
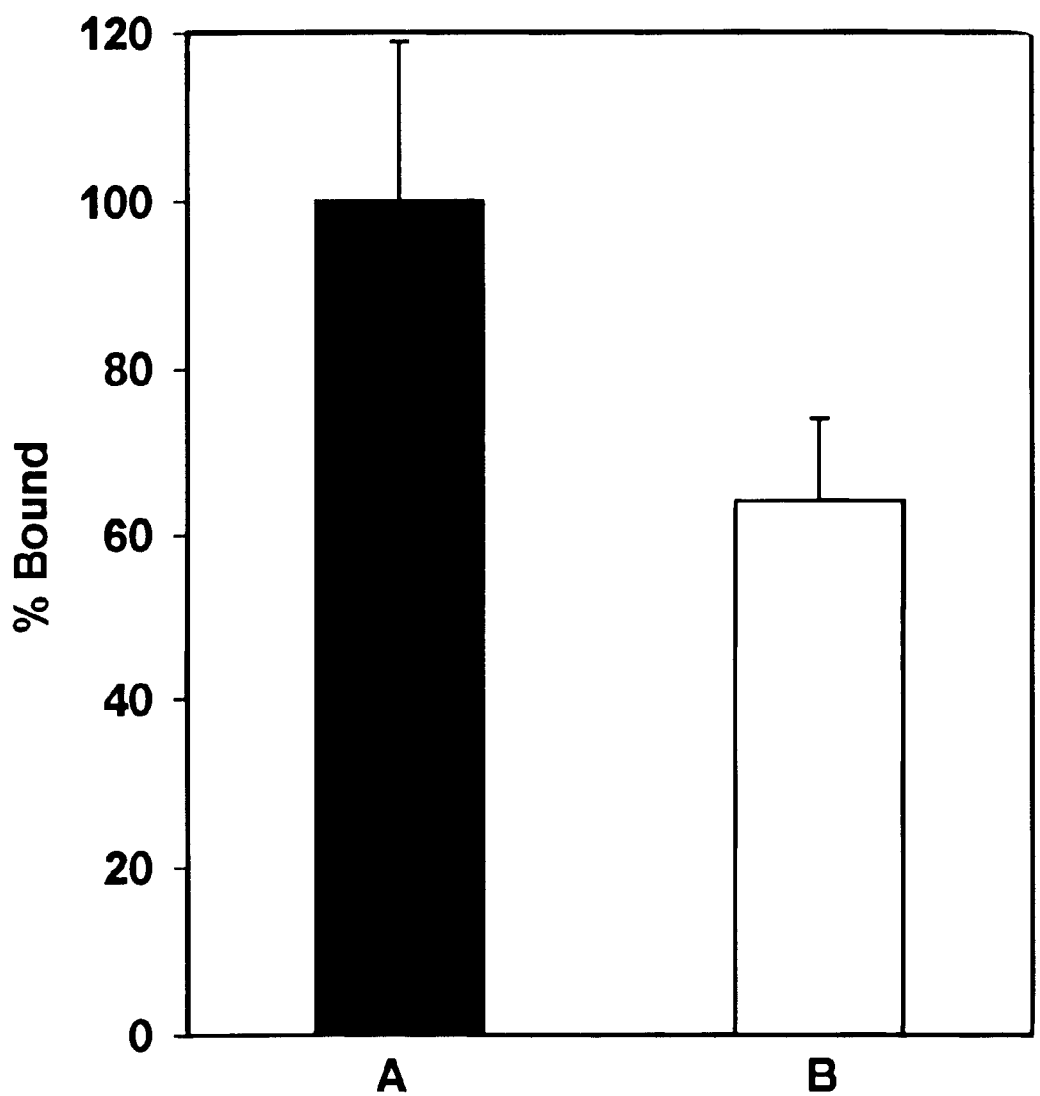
FIG. 6. Competition binding assay between angiostatin and the antibody against the α subunit of ATP synthase from E. coli. HUVEC were plated at a constant density of 10,000 cells/well and incubated with 0.5 μM $^{125}$I-labeled angiostatin in the presence of 1:10 dilution of antibody against the α subunit of ATP synthase from E. coli for 1 h at 4° C. Cells were washed and remaining bound radioactivity was quantified by γ-counting. Non-specific binding was measured in the presence of excess unlabeled angiostatin and was subtracted from total binding. (A) Total binding of 0.5 μM $^{125}$I-labeled angiostatin was designated as 100%. (B) Angiostatin binding is inhibited by 59% in the presence of a 1:10 dilution of anti-α subunit ATP synthase antibody. Competition studies were also performed simultaneously using rabbit pre-immune serum to account for non-specific inhibition. Error bars represent standard deviation. A 1 tailed homoscedastic t test was used for statistical analysis; $p<0.10$.
Figure 7:
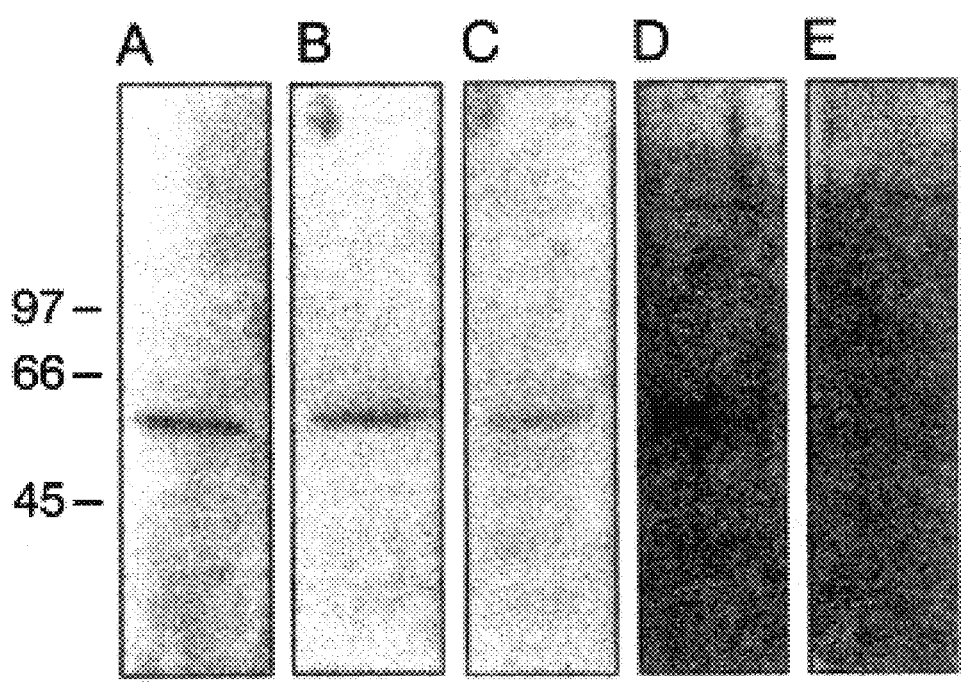
FIGS. 7A–7E. Angiostatin binding to the recombinant α subunit of human ATP synthase. The α subunit of human ATP synthase was cloned and expressed in E. coli and purified using Qiagen's nickel-Sepharose protein purification system before dialyzing in PBS, pH 7.0. Recombinant protein was electrophoresed on 5–15% SDS-PAGE, electroblotted onto Immobilon™ membrane and incubated 18 h in 10 mM Tris-HCl, 0.15M NaCl, 0.05% NP40, pH 7.5 (TSN) containing $^{125}$I-angiostatin. For competition studies unlabeled ligand was added 4 h prior to radiolabeled ligand. Blots were washed in TSN buffer containing 0.05% Tween80 and bound radioactivity was quantified on a Molecular Dynamics PhosphorImager™.
Figure 8:
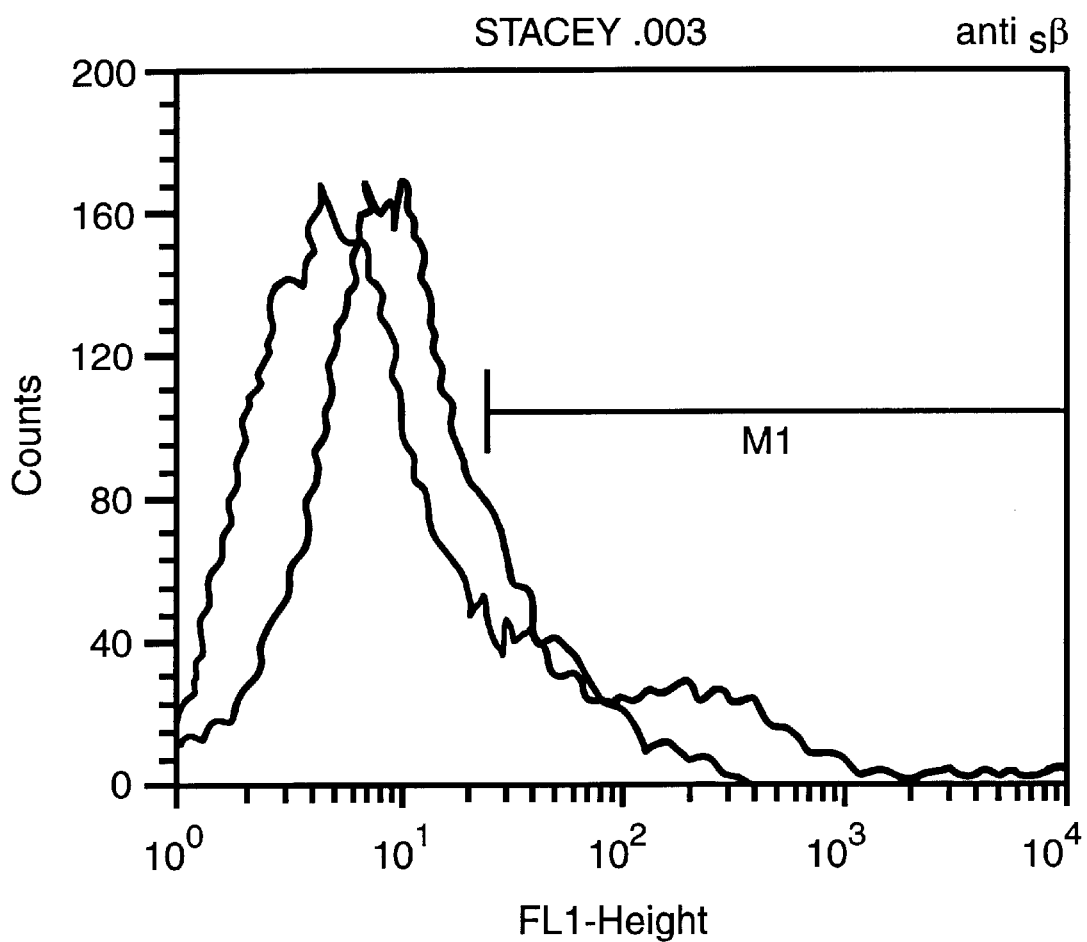
FIG. 8. Binding of antibody directed against the β subunit of ATP synthase on the surface of HUVEC by flow cytometry. HUVEC were analyzed by FACScan Flow Cytometry as described above and in the Examples. Histogram plots are shown for HUVEC cells incubated with antibody directed against the β subunit of ATP synthase.

Inhibition of Angiostatin Binding in the Presence of the Antibody to the α Subunit of ATP Synthase The rabbit polyclonal antiserum raised against the α subunit ATP synthase blocked binding of angiostatin to HUVEC by 59%, demonstrating that this protein functions in angiostatin binding (FIG. 6). In addition, $^{125}$I-labeled angiostatin bound to purified recombinant α subunit from human ATP synthase (FIG. 7B) and binding was inhibited ~56% in the presence of a 250-fold molar excess of unlabeled angiostatin (FIG. 7C). Complete inhibition of binding was not obtained and may be due in part to non-specific binding, improper folding of the recombinant protein or binding epitopes only found in the presence of the α/β heterodimer. Furthermore, binding to the recombinant α subunit ATP synthase was not inhibited by a 2500-fold molar excess of unlabeled plasminogen (FIG. 7D). Further, $^{125}$I-labeled plasminogen did not bind to the recombinant α subunit ATP synthase (FIG. 7E), but did bind to annexin II (FIG. 3D).

EXAMPLE 6

Inhibition of Proliferation in the Presence of Antibody to the α Subunit of Human ATP Synthase To determine whether the anti-proliferative effects of angiostatin were mediated by ATP synthase binding, cell proliferation assays were performed in the presence of antiserum raised against the α subunit of ATP synthase from E. coli. The inhibitory effects of angiostatin on HUVEC proliferation were abrogated by ~81% in the presence of antibody to the α subunit of ATP synthase (Table II), providing direct evidence that angiostatin binding to the α subunit of ATP synthase functions as a mechanism for inhibition of endothelial cell growth. These data indicated that this binding site serves as a receptor for angiostatin.

TABLE II

The anti-proliferative effect of angiostatin is reversed by anti-α subunit ATP synthase antibody.

| Concentration | Percent proliferation inhibited, +/− SEM | | |
| --- | --- | --- | --- |
| angiostatin added, μM | Without antibody | With antibody | % Recovery |
| 0 | 0 | 0 | 0 |
| 0.5 | 10 ± 1.4 | 1 ± 0.2 | 90 |
| 0.75 | 25 ± 4.2 | 5 ± 4.1 | 80 |
| 1.0 | 23 ± 9.0 | 6 ± 0.8 | 74 |

HUVEC were plated at a density of 5000 cells/well in media containing angiostatin at a final concentration of 0.5, 0.75 and 1.0 μM. Anti-α subunit ATP synthase antibody derived from E. coli was added concomitantly at a dilution of 1:10. MTS/PMS solution was added and absorbance of formazan was quantitated according to the manufacturer's specifications (Promega, Madison, Wis.). The average proliferative effect of pre-immune serum and anti-α subunit antibody alone increased 4.6% over buffer control. Results represent three separate experiments performed in duplicate with S.E.M. Percent recovery represents the ability of the anti-α subunit ATP synthase antibody to block the antiproliferative effect of angiostatin, and thereby restore proliferation to an average of 81% of that obtained with the control cells.

ATP synthase is composed of two functional domains termed $F_1$ and $F_0$. The $F_1$ portion contains multiple subunits ($α_3β_3γδε$) and acts as the catalytic site for ATP synthesis, while the membrane embedded $F_0$ portion is a proton channel (Penefsky et al, Advances in Enzymology and Related Areas of Molecular Biology 64:173–214 (1991)). Isolated α and β subunits bind ATP and have weak ATPase activity; however, ATP synthesis requires all $F_1$ and $F_0$ subunits (Boyer, Ann. Rev. Biochem, 66:717–749 (1997)).

Endothelial cells play a strategic role within the vasculature, serving as a barrier between the intravascular compartment and the underlying tissues and are often exposed to hypoxic stress. Relative to other cell types, endothelial cells are more resistant to hypoxic challenge by their ability to maintain a high level of intracellular ATP (Graven et al, Kidney International 51:426–437 (1997)). A plasma membrane-associated ATP synthase may produce extracellular ATP which can diffuse back into the cell providing an additional, albeit limited, ATP source (Unno et al, Am. J. Physiol. 270:g1010 (1996), Unno et al, Surgery 121:668 (1997)). Angiostatin, by binding to the α/β subunits of plasma membrane-localized ATP synthase, may disrupt this production of ATP, rendering endothelial cells more vulnerable to hypoxic challenge and eventual irreversible cell damage. In the microenvironment of a growing tumor, tissue hypoxia provides a powerful stimulus for the production of angiogenic growth factors such as VEGF, bFGF, and angiopoetin. The ability of host endothelial cells to respond to these growth factors by increased proliferation is likely dependent on the ability to survive hypoxic challenge. By abolishing the ability to resist low oxygen tension, angiostatin may decrease endothelial cell survival in the tumor microenvironment. It has recently been reported that angiostatin may also function by inducing endothelial cell apoptosis, providing an additional independent mechanism for the anti-angiogenic action of this polypeptide (Claesson-Welsh et al, Proc. Natl. Acad. Sci., 95:5579–5583 (1998)).

EXAMPLE 7

Binding of Antibody Directed Against the β Subunit of ATP Synthase on the Surface of HUVEC by Flow Cytometry HUVEC cells were resuspended in ice-cold staining buffer (HBSS, 1% BSA, 0.1% sodium azide) and incubated on ice for 30 min with either rabbit polyclonal anti-serum raised against β subunit ATP synthase derived from E. coli or pre-immune rabbit serum. Cells were washed with ice-cold staining buffer and pelleted in a microfuge at 4° C. This wash was repeated twice and the cells resuspended in ice-cold staining buffer prior to incubation on ice for 30 min in the dark with goat anti-rabbit IgG conjugated to fluorescein isothiocyanate (FITC). Following the final wash (as above), the cells were pelleted and fixed in 10% neutral buffered formalin at a density of $1×10^6$ cells/ml. Control experiments were performed using antibody directed against the β subunit of ATP synthase which was preincubated with a 5-fold molar excess of recombinant β subunit ATP synthase protein. The mean relative fluorescence following excitation at a wavelength of 488 nm was determined for each sample on a FACScan flow cytometer (Becton-Dickenson) and analyzed with CellQuest software (Becton-Dickenson).

All documents cited above are hereby incorporated in their entirety by reference.

One skilled in the art will appreciate from a reading of this disclosure that various changes in form and detail can be made without departing from the true scope of the invention.

What is claimed is:

1. A method of screening a test compound for its ability to inhibit or enhance the binding of angiostatin to ATP synthase comprising:

i) contacting said test compound and angiostatin with ATP synthase, or alpha and/or beta subunits thereof, under conditions such that angiostatin can bind to said ATP synthase, or alpha and/or beta subunits thereof, in the absence of said test compound, and ii) determining the amount of angiostatin bound to said ATP synthase, or alpha and/or beta subunits thereof, and comparing that amount of an amount of angiostatin bound to said ATP synthase, or alpha and/or beta subunits portion thereof, in the absence of said test compound, wherein a reduction in the amount of angiostatin bound to said ATP synthase, or alpha and/or beta subunits thereof, in the presence of said test compound indicates that said test compound inhibits the binding of angiostatin to said ATP synthase, or alpha and/or beta subunits thereof, and wherein an increase of the amount of angiostatin bound to said ATP synthase, or alpha and/or beta subunits thereof, in the presence of said test compound indicates that said test compound enhances the binding of angiostatin to said ATP synthase, or alpha and/or beta subunits thereof.

2. The method of claim 1 wherein said angiostatin bears a detectable label.

3. The method of claim 1 wherein said ATP synthase, or alpha and/or beta subunits thereof, is attached to a solid support.

4. The method of claim 1 wherein said ATP synthase, or alpha and/or beta subunits thereof, is associated with a lipid membrane.

5. The method of claim 4 wherein said membrane is a membrane of an intact cell.

6. The method of claim 5 wherein said cell naturally expresses ATP synthase.

7. The method of claim 5 wherein said cell has been transformed with a nucleic acid sequence that enclosed said ATP synthase, or alpha and/or beta subunits thereof.

8. A method of screening a test compound for its ability to promote or inhibit angiogenesis resulting from binding of angiostatin to ATP synthase comprising:

i) contacting said test compound and angiostatin with a cell that expresses ATP synthase, or alpha and/or beta subunits thereof, under conditions such that angiostatin can bind to said ATP synthase, or alpha and/or beta subunits thereof, in the absence of said test compound, and ii) determining the amount of angiostatin required to achieve the same effect on angiogenesis in the presence of said test compound as in the absence of said test compound, wherein a reduction in the amount of angiostatin required to achieve the same effect on angiogenesis in the presence of said test compound indicates that said test compound is an angiostatin agonist, and wherein an increase of the amount of angiostatin required to achieve the same effect on angiogenesis in the presence of said test compound indicates that said test compound is an angiostatin antagonist.

9. The method of claim 8, wherein said inhibition of angiogenesis results in the inhibition of cell proliferation.

10. A method of screening a test compound for its ability to inhibit or enhance proton pumping resulting from binding of angiostatin to ATP synthase comprising:

i) contacting said test compound and angiostatin with a cell that expresses ATP synthase, or alpha and/or beta subunits thereof, under conditions such that angiostatin can bind to said ATP synthase, or alpha and/or beta subunits thereof, in the absence of said test compound, and ii) determining the amount of angiostatin required to achieve the same effect on proton pumping in the presence of said test compound as in the absence of said test compound, wherein a reduction in the amount of angiostatin required to achieve the same effect on proton pumping in the presence of said test compound indicates that said test compound is an angiostatin agonist, and wherein an increase of the amount of angiostatin required to achieve the same effect on proton pumping in the presence of said test compound indicates that said test compound is an angiostatin antagonist.

* * * * *